United States Patent
Xu et al.

(10) Patent No.: US 12,017,217 B2
(45) Date of Patent: Jun. 25, 2024

(54) MULTI-CHANNEL MICROFLUIDIC CHIP HAVING FIVE-LAYER STRUCTURE

(71) Applicant: LANSION BIOTECHNOLOGY CO., LTD., Jiangsu (CN)

(72) Inventors: Xingshang Xu, Jiangsu (CN); Jeffery Chen, Jiangsu (CN)

(73) Assignee: LANSION BIOTECHNOLOGY CO., LTD., Jiangsu (CN)

( * ) Notice: Subject to any disclaimer, the term of this patent is extended or adjusted under 35 U.S.C. 154(b) by 455 days.

(21) Appl. No.: 17/435,399

(22) PCT Filed: Apr. 13, 2020

(86) PCT No.: PCT/CN2020/084386
§ 371 (c)(1),
(2) Date: Sep. 1, 2021

(87) PCT Pub. No.: WO2020/177773
PCT Pub. Date: Sep. 10, 2020

(65) Prior Publication Data
US 2022/0143609 A1   May 12, 2022

(30) Foreign Application Priority Data
Mar. 1, 2019  (CN) .......................... 201910154636.4

(51) Int. Cl.
*B01L 3/00*   (2006.01)
*G01N 27/327*   (2006.01)

(52) U.S. Cl.
CPC .... *B01L 3/502715* (2013.01); *G01N 27/3272* (2013.01); *B01L 2200/027* (2013.01);
(Continued)

(58) Field of Classification Search
None
See application file for complete search history.

(56) References Cited

U.S. PATENT DOCUMENTS

| 2008/0124749 A1* | 5/2008 | Farnam ................... C12Q 1/56 |
| | | 422/68.1 |
| 2010/0175993 A1 | 7/2010 | Lee et al. |

(Continued)

FOREIGN PATENT DOCUMENTS

| CN | 103913489 | 7/2014 |
| CN | 108398470 | 8/2018 |

(Continued)

OTHER PUBLICATIONS

"International Search Report (Form PCT/ISA/210)" of PCT/CN2020/084386, with English translation thereof, mailed on Jul. 1, 2020, pp. 1-5.

(Continued)

*Primary Examiner* — P. Kathryn Wright
(74) *Attorney, Agent, or Firm* — JCIP GLOBAL INC.

(57) ABSTRACT

A multi-channel microfluidic blood coagulation detection chip having a five-layer structure includes a chip body. The chip body includes, in sequence from top to bottom, a first-layer chip, a second-layer chip, a third-layer chip, a fourth-layer chip, and a fifth-layer chip. The first-layer chip (1), the second-layer chip, the third-layer chip, the fourth-layer chip, and the fifth-layer chip cooperate with each other to define a closed microfluidic channel and a plurality of mutually-independent detection chambers. The first-layer chip is provided with a sample loading hole, and the sample loading hole communicates with the detection chambers through the microfluidic channel. The chip body further includes electrodes, and the electrodes are disposed within the detection chambers in one-to-one correspondence.

12 Claims, 5 Drawing Sheets

(52) U.S. Cl.
CPC .............. *B01L 2200/0647* (2013.01); *B01L 2200/0684* (2013.01); *B01L 2200/141* (2013.01); *B01L 2200/16* (2013.01); *B01L 2300/0645* (2013.01); *B01L 2300/0663* (2013.01); *B01L 2300/0864* (2013.01)

(56) References Cited

U.S. PATENT DOCUMENTS

2017/0052169 A1* 2/2017 Zhang ................ G01N 33/4905
2021/0086179 A1* 3/2021 Xu .................... B01L 3/502715

FOREIGN PATENT DOCUMENTS

| CN | 108452854 | 8/2018 | | |
| CN | 108452856 A | * 8/2018 | ................ | B01L 3/00 |
| CN | 108745429 | 11/2018 | | |
| CN | 109358101 | 2/2019 | | |
| CN | 109682878 | 4/2019 | | |
| CN | 209640280 | 11/2019 | | |

OTHER PUBLICATIONS

"Written Opinion of the International Searching Authority (Form PCT/ISA/237)" of PCT/CN2020/084386, mailed on Jul. 1, 2020, pp. 1-5.

* cited by examiner

MULTI-CHANNEL MICROFLUIDIC CHIP HAVING FIVE-LAYER STRUCTURE

CROSS-REFERENCE TO RELATED APPLICATION

This application is a 371 of international application of PCT application serial no. PCT/CN2020/084386, filed on Apr. 13, 2020 which claims the priority benefit of China application no. 201910154636.4, filed on Mar. 1, 2019. The entirety of each of the above mentioned patent applications is hereby incorporated by reference herein and made a part of this specification.

BACKGROUND

Technical Field

The present invention relates to the technical field of medical devices, and in particular, to a multi-channel microfluidic blood coagulation detection chip having a five-layer structure.

Description of Related Art

Microfluidics is a technology applied across various disciplines including engineering, physics, chemistry, microtechnology, and biotechnology. Microfluidics involves the study of micro-fluids and the study of how to manipulate, control and use such small volumes of fluids in various microfluidic systems and devices such as microfluidic chips. For example, microfluidic biochips (referred to as "lab-on-a-chip") are used in the field of molecular biology to integrate assay operations for purposes such as analyzing enzymes and DNA, detecting biochemical toxins and pathogens, and diagnosing diseases.

Microfluidic chip relates to a hot field in the current development of miniaturized total analysis systems. Microfluidic chip analysis takes a chip as an operating platform, analytical chemistry as the basis, a micro-electromechanical processing technology as the support, a micro-pipeline network as a structural feature, and life sciences as the main application object at present, and is the focus of the current development in the field of miniaturized total analysis systems. The goal of the microfluidic chip analysis is to integrate the functions of the entire laboratory, including sampling, dilution, reagent addition, reaction, separation, and detection, on a microchip. Microfluidic chip is the main platform for the realization of microfluidic technologies. Main device features of the microfluidic chip are that the effective structures (channels, detection chambers and some other functional components) containing fluids are micron-scale-sized in at least one dimension. Due to the micron-scale structure, the fluid exhibits and produces special properties therein that are different from those at the macro scale. Therefore, unique analysis-generated properties have been developed. Features and development advantages of the microfluidic chip are as follows. The microfluidic chip is characterized by controllable liquid flow, minimal consumption of samples and reagents, and an increase in analysis speed by ten times or hundreds of times; and simultaneous analysis of hundreds of samples can be performed in a few minutes or even less, and the entire process of sample pretreatment and analysis can be realized online. The application purpose of the microfluidic chip is to achieve the ultimate goal of the miniaturized total analysis systems, i.e., the lab-on-a-chip, and the key application field of current work development is the field of life sciences.

Current international research status are as follows. Innovations are mostly focused on separation and detection systems, and the research on a number of issues about how to introduce actual samples for analysis on the chip, such as sample introduction, sample change, and pretreatment, is still very weak. The development depends on interdisciplinary development.

Chinese patent publication of CN108398470A discloses a biosensor for blood activated clotting time determination, including a bottom layer, a middle layer, and an upper layer stacked and connected in sequence. The upper layer is provided with a sample loading channel and a ventilation channel, and both the sample loading channel and the ventilation channel run through the upper layer in the thickness direction. The middle layer is provided with at least one sample deposition hole, at least one diffusion channel, and at least one detection cell. The detection cell communicates with the sample deposition hole through the diffusion channel, and the detection cell runs through the middle layer in the thickness direction. The upper surface of the bottom layer is provided with a working electrode and a reference electrode. The sample loading channel is located above the sample deposition hole and communicates with the sample deposition hole. The ventilation channel is located above the detection cell and communicates with the detection cell. The surface regions of the bottom layer and the upper layer facing and corresponding to the detection cell cooperate with the cell wall of the detection cell to enclose a sample detection cavity. One ends of both the working electrode and the reference electrode are located in the sample detection cavity, and the other ends of both the working electrode and the reference electrode extend beyond the middle layer and the upper layer to form connection ends to connect to a detection instrument. Both an upper cavity wall of the sample detection cavity and a lower cavity wall between the working electrode and the reference electrode are provided with a dry clotting promoter coating. In the biosensor for blood activated clotting time determination, although multiple channels and multiple detection chambers are designed for simultaneous detection, the multiple detection chambers use the same reference electrode, and the reference electrode and the working electrode are both designed on the bottom layer. The interference between the electrodes designed in this way is great, which may affect the accuracy of sample detection results in an actual detection process.

Chinese patent document (application no. 201810599700.5) discloses a microfluidic detection chip for multi-channel rapid detection, including a chip body. A chip sampling port, a plurality of mutually-independent detection chambers, and a microfluidic channel are disposed on the chip body, and the chip sampling port communicates with the detection chambers through the microfluidic channel. The chip body further includes electrodes, and the detection chambers are connected to the electrodes. The microfluidic channel includes a main flow channel and a plurality of branching microfluidic channels. The tail end of the main flow channel is divided into the plurality of branching microfluidic channels, and the plurality of branching microfluidic channels communicate in one-to-one correspondence with the plurality of mutually-independent detection chambers. The other end of the main flow channel communicates with the chip sampling port. The microfluidic detection chip for multi-channel rapid detection is a three-layer chip, and the size of the chip body is about 8~10 cm*2.4~2.8 cm, and therefore, the size of the chip is too large.

Therefore, it is necessary to develop a multi-channel microfluidic blood coagulation detection chip having a five-layer structure, which has large detection throughput, high detection efficiency and accuracy, as well as smaller size and lower cost.

SUMMARY

The technical problem to be solved by the present invention is to provide a multi-channel microfluidic blood coagulation detection chip having a five-layer structure, which is reasonable in design and has large detection throughput, high detection efficiency and accuracy, as well as smaller size and lower cost.

In order to solve the above-mentioned technical problem, the technical solution adopted in the present invention is that, a multi-channel microfluidic blood coagulation detection chip having a five-layer structure, including a chip body. The chip body includes, in sequence from top to bottom, a first-layer chip, a second-layer chip, a third-layer chip, a fourth-layer chip, and a fifth-layer chip. The first-layer chip, the second-layer chip, the third-layer chip, the fourth-layer chip, and the fifth-layer chip cooperate with each other to define a closed microfluidic channel and a plurality of mutually-independent detection chambers. The first-layer chip is provided with a sample loading hole, and the sample loading hole communicates with the detection chambers through the microfluidic channel. The chip body further includes electrodes, and the electrodes are disposed within the detection chambers in one-to-one correspondence.

By using the above-mentioned technical solution, microfluidic chip detection has the characteristics of high accuracy, fast speed and low detection cost, and is suitable for detection in precision medical links. By designing the five layers of chips to cooperate to define the closed microfluidic channel and the plurality of mutually-independent detection chambers, it is possible to detect multiple sample indexes simultaneously. Through the design of the five layers of chips, the number of the detection chambers can be multiplied, so that more coagulation indexes can be detected at a time, and the detection efficiency is improved. The design is reasonable, the structure is simple and compact, and the production cost can be lowered as the number of the detection chambers is multiplied. A detection reagent is pre-embedded in each detection chamber, and signals generated by blood reaction in the detection chambers are received while applying an alternating-current voltage. The chip is simple in structure and easy to operate, improves the detection efficiency, and greatly reduces the consumption of resources. Thus, quick detection is realized, and the cost is lowered.

The further improvement of the present invention is that, both the microfluidic channel and the detection chambers run through the second-layer chip and the fourth-layer chip. The microfluidic channel includes a main flow channel and a plurality of branching microfluidic channels, the tail end of the main flow channel is divided into the plurality of branching microfluidic channels, and the plurality of branching microfluidic channels communicate in one-to-one correspondence with the plurality of mutually-independent detection chambers; and the front end of the main flow channel communicates with the sample loading hole. Designing the main flow channel and the plurality of branching microfluidic channels in a specific structural form to guide the flow of a blood sample allows for simultaneous injection of the sample into a plurality of reaction chambers through one main flow channel and the plurality of branching microfluidic channels without contaminating the sample, thereby facilitating sample injection. After the sample is injected from the sample loading hole, the sample flows from the main flow channel to the plurality of branching microfluidic channels simultaneously, and then enters the plurality of mutually-independent detection chambers. Each detection chamber is formed by a branching microfluidic channel extending to both ends outwards on the tail end thereof, that is, the width of the detection chamber is greater than the width of the branching microfluidic channel connected thereto. Such a setting allows the test sample to flow to the detection chambers easier and faster. Moreover, detection reagents are pre-embedded in the detection chambers, so that multiple indexes can be detected simultaneously, and a multi-channel effect is achieved. The chip is simple in structure and easy to operate, improves the detection efficiency, and greatly reduces the consumption of resources. Thus, quick detection is realized, and the cost is lowered.

The further improvement of the present invention is that, both the first-layer chip and the fifth-layer chip are provided with a plurality of vent holes, and the plurality of vent holes are all disposed in one ends of the first-layer chip and the fifth-layer chip at positions corresponding to the detection chambers and correspond one-to-one to the plurality of detection chambers. By providing the plurality of vent holes that run through the upper-layer chip, the flow resistance of the fluid to be tested is reduced, so that the flow is faster, and the detection chambers can be quickly filled. The setting of the vent holes facilitates the flow of the sample and is convenient for sample injection. If there is no vent hole, the sample cannot flow into the detection chambers for reaction, and the detection reagents are pre-embedded in the detection chambers. In addition, the setting of the vent holes in the fifth layer does not cause leakage of the whole blood sample, because blood is thicker and its flow requires the cooperation of hydrophilic interfaces on both sides. The positions of the vent holes are tangent to the tail ends (i.e., the ends away from the branching microfluidic channels) of the detection chambers. When the blood flows to the positions, the hollow setting of the vent holes enables the blood to only contact the hydrophilic interface on one side, thus the blood does not continue to flow forward and leak.

The further improvement of the present invention is that, the electrodes are disposed on the third-layer chip or disposed on the third-layer chip and the fifth-layer chip. The electrodes include reference electrodes and working electrodes, and the reference electrodes and the working electrodes are disposed within the detection chambers in one-to-one correspondence. Providing both a reference electrode and a working electrode in each detection chamber can effectively ensure the consistency of detection results of all the detection chambers.

As a preferred technical solution of the present invention, both the working electrodes and the reference electrodes are disposed on the third-layer chip, or disposed on the third-layer chip and the fifth-layer chip. One ends of both the working electrodes and the reference electrodes are located within the detection chambers, and the other ends of both the working electrodes and the reference electrodes extend to an end head of the third-layer chip or end heads of the third-layer chip and the fifth-layer chip to form detection ends. The plurality of detection chambers corresponding to the branching microfluidic channels are each independently provided therein with one of the working electrodes, which are independently led out to the detection ends. The reference electrodes in the plurality of detection chambers corresponding to the branching microfluidic channels are all connected together in series and then led out to the detection ends. Connecting the reference electrode in each detection chamber together in series, and further enabling each reference electrode and each working electrode to perform resistance measurement at the same position in each detection chamber better facilitate ensuring the consistency of the detection results of all the detection chambers. Both the reference electrodes and the working electrodes are rectangular at the detection ends and arranged flush with the end head of the third-layer chip or/and the fifth-layer chip.

The further improvement of the present invention is that, the reference electrodes include a first reference electrode and a second reference electrode, the first reference electrode is separated from the second reference electrode, the first reference electrode is disposed on the front surface of the third-layer chip, and the second reference electrode is disposed on the back surface of the third-layer chip or the front surface of the fifth-layer chip.

The further improvement of the present invention is that, the working electrodes include a first working electrode and a second working electrode, the first working electrode is separated from the second working electrode, the first working electrode is disposed on the front surface of the third-layer chip, and the second working electrode is disposed on the back surface of the third-layer chip or the front surface of the fifth-layer chip.

As a preferred technical solution of the present invention, one end of the first working electrode and one end of the first reference electrode are both located within the detection chambers on the front surface of the third-layer chip; and the other end of first working electrode and the other end of the first reference electrode both extend beyond the end heads of one end of the first-layer chip and one end of the second-layer chip on the front surface of the third-layer chip and form a first detection end that is connected to a detection instrument. The first working electrode and the first reference electrode are arranged in one-to-one correspondence with the detection chambers on the second-layer chip, to ensure the collection and detection of electrochemical signals of the detection chambers on the second-layer chip.

As a preferred technical solution of the present invention, one end of the second reference electrode and one end of the second working electrode are both located within the detection chambers; and the other end of the second reference electrode and the other end of the second working electrode both extend beyond the end heads of one end of the fourth-layer chip and one end of the fifth-layer chip on the back surface of the third-layer chip and form a second detection end that is connected to the detection instrument, or the other end of the second reference electrode and the other end of the second working electrode both extend beyond the end heads of one end of the third-layer chip and one end of the fourth-layer chip on the front surface of the fifth-layer chip and form a third detection end that is connected to the detection instrument. The second working electrode and the second reference electrode are arranged in one-to-one correspondence with the detection chambers on the fourth-layer chip, to ensure the collection and detection of electrochemical signals of the detection chambers on the fourth-layer chip.

As a preferred technical solution of the present invention, the third detection end is exposed outside the end head of the first detection end. Such a setting can avoid interference between the first working electrode as well as the first reference electrode on the third-layer chip and the second working electrode as well as the second reference electrode on the fifth-layer chip, and enable the first detection end and the third detection end of the multi-channel microfluidic blood coagulation detection chip having a five-layer structure to be directly connected to the detection instrument simultaneously after the detection chip is inserted into the detection instrument.

The further improvement of the present invention is that, every two adjacent branching microfluidic channels among the plurality of branching microfluidic channels corresponding to the main flow channel are of different lengths, so that the plurality of detection chambers to which the plurality of adjacent branching microfluidic channels are connected are arranged in a staggered distribution. Such a setting can decrease the size of the chip body and lower the cost.

As a preferred technical solution of the present invention, the second-layer chip is provided with a first liquid receiving port, the third-layer chip is provided with a second liquid receiving port, the fourth-layer chip is provided with a third liquid receiving port, and the first liquid receiving port, the second liquid receiving port and the third liquid receiving port are all arranged corresponding to the position of the sample loading hole and all communicate with the sample loading hole. The first main flow channel includes a first main flow channel and a second main flow channel. Each branching microfluidic channel includes a first branching microfluidic channel and a second branching microfluidic channel. The first main flow channel and the first branching microfluidic channel run through the second-layer chip. The second main flow channel and the second branching microfluidic channel run through the fourth-layer chip. One end of the first main flow channel is connected to the first liquid receiving port, and the other end of the first main flow channel is connected to the plurality of detection chambers through a plurality of the first branching microfluidic channels in one-to-one correspondence; and one end of the second main flow channel is connected to the third liquid receiving port, and the other end of the second main flow channel is connected to the plurality of detection chambers through a plurality of the second branching microfluidic channels in one-to-one correspondence. After entering the chip through the sample loading hole, a test sample flows to the first main flow channel and the second liquid receiving port separately through the first liquid receiving port, flows to the third liquid receiving port through the second liquid receiving port, and flows to the second main flow channel through the third liquid receiving port, so as to simultaneously flow to the detection chambers of the second-layer chip and the detection chambers of the fourth-layer chip, separately.

As a preferred technical solution of the present invention, the first main flow channel extends in a horizontal direction to the end away from the first liquid receiving port to be provided with a first part of the first branching microfluidic channel that is connected to a first detection chamber; the first main flow channel extends in a vertical direction to the end away from the first liquid receiving port towards both sides respectively to be provided with a second part of the first branching microfluidic channel and a second part of the first branching microfluidic channel. the second part of the first branching microfluidic channel extends in a direction parallel to the first main flow channel to both ends respectively to connect to a second detection chamber and a third detection chamber; and the third part of the first branching microfluidic channel extends in the direction parallel to the first main flow channel to both ends respectively to connect to a fourth detection chamber and a fifth detection chamber. Designing the main flow channel and the plurality of branching microfluidic channels in a specific structural form to guide the flow of a blood sample allows for simultaneous injection of the sample from one sample chamber into a plurality of reaction chambers, which makes the flow faster and improves the detection efficiency. In addition, such a design decreases the size of the multi-channel microfluidic blood coagulation detection chip having a five-layer structure. Compared with the multi-channel microfluidic blood coagulation detection chip of a three-layer structure previously claimed by the applicant, the length and width are decreased by 25%~45%, therefore, the production cost is lowered, and the chip is smaller and more portable.

As a preferred technical solution of the present invention, the second main flow channel extends in a horizontal direction to the end away from the third liquid receiving port to be provided with a first part of the second branching microfluidic channel that is connected to a sixth detection chamber; the second main flow channel extends in a vertical direction to the end away from the third liquid receiving port towards both sides respectively to be provided with a second part of the second branching microfluidic channel and a third part of the second branching microfluidic channel. The second part of the second branching microfluidic channel extends in a direction parallel to the second main flow channel to both ends respectively to connect to a seventh detection chamber and an eighth detection chamber; and the third part of the second branching microfluidic channel extends in the direction parallel to the second main flow channel to both ends respectively to connect to a ninth detection chamber and a tenth detection chamber. Designing the main flow channel and the plurality of branching microfluidic channels in a specific structural form to guide the flow of a blood sample allows for simultaneous injection of the sample from one sample chamber into a plurality of reaction chambers, which makes the flow faster and improves the detection efficiency. In addition, such a design decreases the size of the multi-channel microfluidic blood coagulation detection chip having a five-layer structure. Compared with the multi-channel microfluidic blood coagulation detection chip previously claimed by the applicant, the length and width are decreased by 25%~45%, therefore, the production cost is lowered, and the chip is smaller and more portable.

As a preferred technical solution of the present invention, the sizes of the first liquid receiving port, the second liquid receiving port, and the third liquid receiving port are all greater than or equal to the size of the sample loading hole. The plurality of vent holes are all disposed above positions tangent to the tail ends of the plurality of detection chambers. The number of the vent holes on both the first-layer chip and the fifth-layer chip is five. The tail ends of the detection chambers are the ends far away from the branching microfluidic channels, and each detection chamber is provided with a vent hole.

As a preferred technical solution of the present invention, the shapes of each of the detection ends, the first detection end, the second detection end, and the third detection end are all rectangular, and the spacing among the detection ends is equal.

As a preferred technical solution of the present invention, the first-layer chip, the second-layer chip, the third-layer chip, the fourth-layer chip, and the fifth-layer chip are bonded into an integral whole by means of gluing. Preferably, the first-layer chip, the second-layer chip, the third-layer chip, the fourth-layer chip, and the fifth-layer chip are bonded into an integral whole through double-sided gluing.

As a preferred technical solution of the present invention, the second-layer chip and the fourth-layer chip are pressure-sensitive adhesive tapes. The materials of the first-layer chip, the third-layer chip and the fifth-layer chip are all any one of PMMA, PP, PE, and PET, and the surfaces of the first-layer chip and the fifth-layer chip each are provided with a hydrophilic membrane, so that the sample quickly flows into the main flow channel through the sample loading hole, and then separately flows to each branching microfluidic channel. With this technical solution, materials are easily available, and the manufacturing process of the pressure-sensitive adhesive tapes allows for accurate control of the thicknesses thereof. Therefore, with this technical solution, the depth and size of the microfluidic channel can be accurately controlled, and the depth control of the detection chambers is also facilitated, so that the thickness deviation of each detection chamber of the microfluidic chip is small, the consistency is high, and the detection accuracy is improved. The surfaces of the first-layer chip and the fifth-layer chip each are provided with a hydrophilic membrane, so that the sample quickly flows into the main flow channel through the sample loading hole, and then separately flow to each branching microfluidic channel. In this way, the flow speed is accelerated, and the detection efficiency can be improved.

As a preferred technical solution of the present invention, the thicknesses of the second-layer chip and the fourth-layer chip are both 0.1~1.0 mm. The depths of the closed microfluidic channels defined by the first-layer chip, the second-layer chip and the front surface of the third-layer chip and by the fourth-layer chip, the fifth-layer chip and the back surface of the third-layer chip in cooperation are both 0.1~1.0 mm, and the widths of the detection chambers defined by the five layers of chips in cooperation are all 1.0~2.0 mm.

As a preferred technical solution of the present invention, each of the branching microfluidic channels is provided with a nozzle at a junction with the detection chamber, and the thickness of the electrodes is 0.5 mm. Nozzles are provided at the junctions between the branching microfluidic channels and the detection chambers to enable the sample to flow into the detection chambers more easily and quickly. The function of the electrodes is to receive signals generated by blood reaction in the detection chambers while applying an alternating-current voltage.

Compared with the prior art, by designing the five layers of chips to cooperate to define the closed microfluidic channel and the plurality of mutually-independent detection chambers, it is possible to detect multiple indexes of a sample simultaneously. Through the design of the five layers of chips, the number of the detection chambers can be multiplied, so that more coagulation indexes can be detected at a time. That is, by designing the five layers of chips, there are 10 detection chambers in total, which work in conjunction with the corresponding electrodes, so that 10 coagulation indexes can be detected with one sample injection. The design is reasonable, the structure is simple and compact, and the production cost can be lowered as the number of the detection chambers is multiplied. A detection reagent is pre-embedded in each detection chamber, and signals generated by blood reaction in the detection chambers are received while applying an alternating-current voltage. The chip is simple in structure and easy to operate, improves the detection efficiency, and greatly reduces the consumption of resources. Thus, quick detection is realized, and the cost is lowered. In addition, designing the main flow channel and the plurality of branching microfluidic channels in a specific structural form to guide the flow of a blood sample allows for simultaneous injection of the sample from one sample chamber into a plurality of reaction chambers without contaminating the sample, thereby facilitating sample injection. The size of the multi-channel microfluidic blood coagulation detection chip is decreased. Compared with the multi-channel microfluidic blood coagulation detection chip of a three-layer structure previously claimed by the applicant, the length and width are decreased by 25%~45% (the length and width of the chip claimed previously are 8~10 cm*2.4~2.8 cm, and the length and width of this multi-channel microfluidic blood coagulation detection chip are 5~7 cm*1.6~2.0 cm), therefore, the production cost is lowered, and the chip is smaller and more portable.

BRIEF DESCRIPTION OF THE DRAWINGS

The detailed description is further provided below with reference to the accompanying drawings and embodiments of the present invention.

DESCRIPTION OF THE EMBODIMENTS

Figure 1:
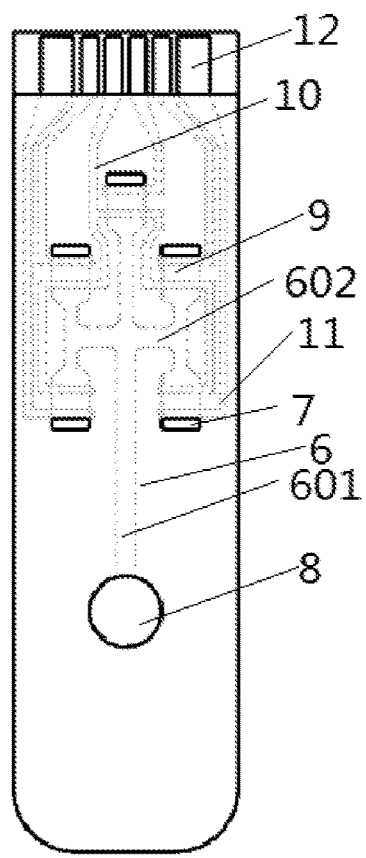
FIG. 1 is a schematic perspective structural diagram of a multi-channel microfluidic blood coagulation detection chip having a five-layer structure according to embodiment 1 of the present invention.
Figure 2:
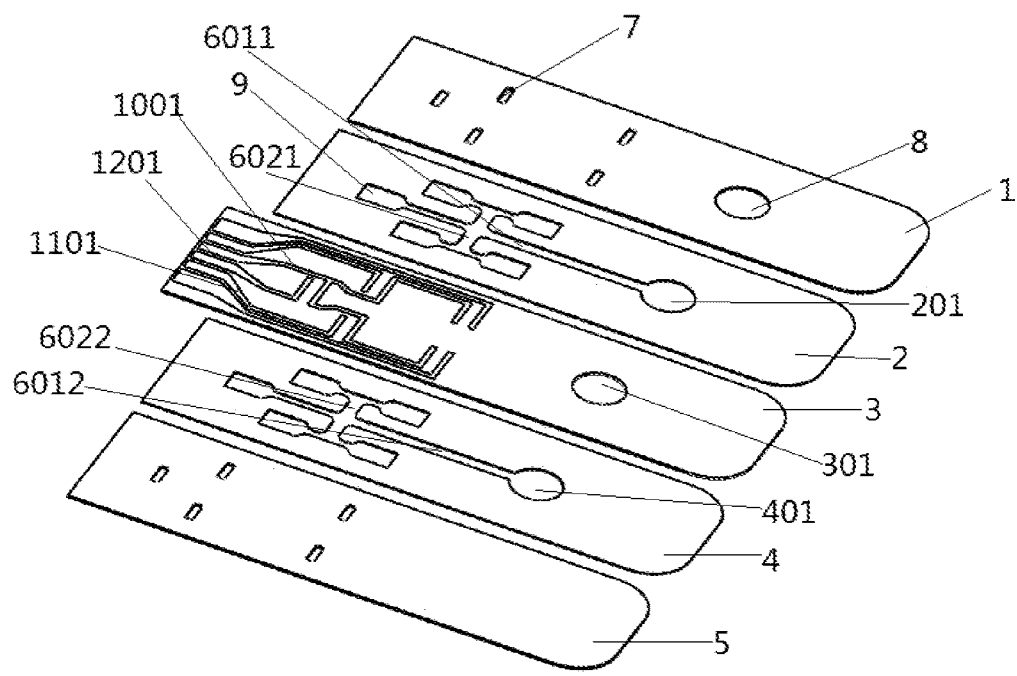
FIG. 2 is a schematic exploded structural diagram of chips of the multi-channel microfluidic blood coagulation detection chip having a five-layer structure according to embodiment 1 of the present invention.
Figure 3:
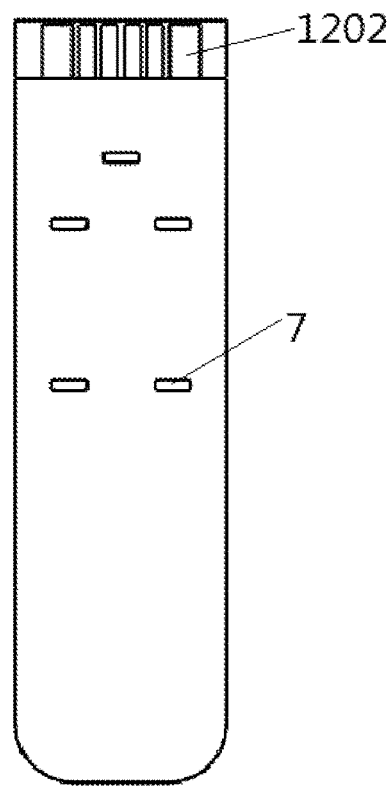
FIG. 3 is a schematic structural diagram of the back surface of the multi-channel microfluidic blood coagulation detection chip having a five-layer structure according to embodiment 1 of the present invention.
Figure 4:
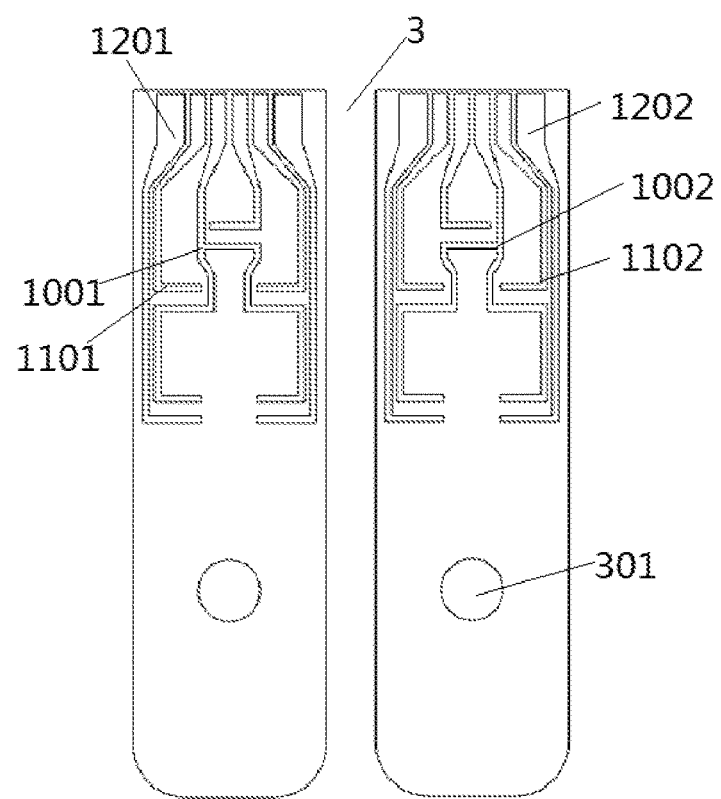
FIG. 4 is a schematic exploded structural diagram of the front surface and the back surface of a third-layer chip of the multi-channel microfluidic blood coagulation detection chip having a five-layer structure according to embodiment 1 of the present invention.
Figure 5:
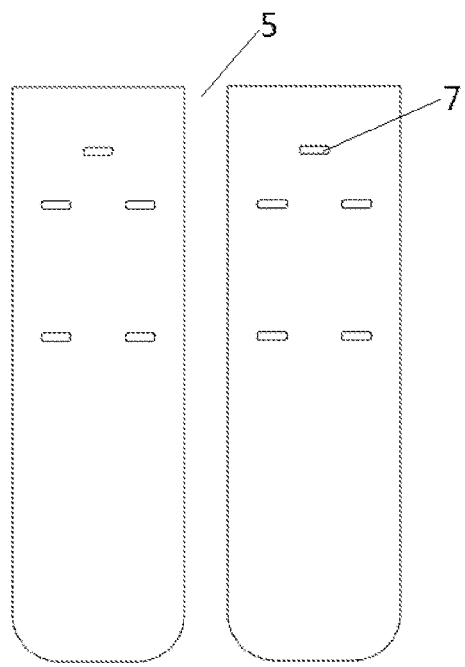
FIG. 5 is a schematic exploded structural diagram of the front surface and the back surface of a fifth-layer chip of the multi-channel microfluidic blood coagulation detection chip having a five-layer structure according to embodiment 1 of the present invention.

Embodiment 1. As shown in FIG. 1 to FIG. 5, the multi-channel microfluidic blood coagulation detection chip having a five-layer structure includes a chip body. The chip body includes, in sequence from top to bottom, a first-layer chip 1, a second-layer chip 2, a third-layer chip 3, a fourth-layer chip 4, and a fifth-layer chip 5. The first-layer chip 1, the second-layer chip 2, the third-layer chip 3, the fourth-layer chip 4, and the fifth-layer chip 5 cooperate with each other to define a closed microfluidic channel and a plurality of mutually-independent detection chambers 9. The first-layer chip 1 is provided with a sample loading hole 8, and the sample loading hole 8 communicates with the detection chambers 9 through the microfluidic channel 6. The chip body further includes electrodes, and the electrodes are disposed within the detection chambers 9 in one-to-one correspondence.

Both the microfluidic channel 6 and the detection chambers 9 run through the second-layer chip 2 and the fourth-layer chip 4. The microfluidic channel 6 includes a main flow channel 601 and a plurality of branching microfluidic channels 602, the tail end of the main flow channel 601 is divided into the plurality of branching microfluidic channels 602, and the plurality of branching microfluidic channels 602 communicate in one-to-one correspondence with the plurality of mutually-independent detection chambers 9. The front end of the main flow channel 601 communicates with the sample loading hole 8. Each detection chamber 9 is formed by a branching microfluidic channel 602 extending to both ends outwards on the tail end thereof, that is, the width of the detection chamber 9 is greater than the width of the branching microfluidic channel 602 connected thereto. Such a setting allows the test sample to flow to the detection chambers 9 easier and faster. Moreover, detection reagents are pre-embedded in the detection chambers 9.

Both the first-layer chip 1 and the fifth-layer chip 5 are provided with a plurality of vent holes 7, and the plurality of vent holes 7 are all disposed in one ends of the first-layer chip 1 and the fifth-layer chip 5 at positions corresponding to the detection chambers 9 and correspond one-to-one to the plurality of detection chambers 9.

The electrodes are disposed on the third-layer chip 3. The electrodes include reference electrodes 10 and working electrodes 11, and the reference electrodes 10 and the working electrodes 11 are disposed within the detection chambers 9 in one-to-one correspondence.

Both the working electrodes 11 and the reference electrodes 10 are disposed on the third-layer chip 3. One ends of both the working electrodes 11 and the reference electrodes 10 are located within the detection chambers 9, and the other ends of both the working electrodes 11 and the reference electrodes 10 extend to an end head of the third-layer chip 3 to form detection ends 12. The plurality of detection chambers 9 corresponding to the branching microfluidic channels 602 are each independently provided therein with one of the working electrodes 11, which are independently led out to the detection ends 12. The reference electrodes 10 in the plurality of detection chambers 9 corresponding to the branching microfluidic channels 602 are all connected together in series and then led out to the detection ends 12. Both the reference electrodes 10 and the working electrodes 11 are rectangular at the detection ends 12 and arranged flush with the end head of the third-layer chip 3.

The reference electrodes 10 include a first reference electrode 1001 and a second reference electrode 1002, the first reference electrode 1001 is separated from the second reference electrode 1002, the first reference electrode 1001 is disposed on the front surface of the third-layer chip 3, and the second reference electrode 1002 is disposed on the back surface of the third-layer chip 3.

The working electrodes 11 include a first working electrode 1101 and a second working electrode 1102, the first working electrode 1101 is separated from the second working electrode 1102, the first working electrode 1101 is disposed on the front surface of the third-layer chip 3, and the second working electrode 1102 is disposed on the back surface of the third-layer chip 3.

One end of the first working electrode 1101 and one end of the first reference electrode 1001 are both located within the detection chambers 9 on the front surface of the third-layer chip 3, and the other end of first working electrode 1101 and the other end of the first reference electrode 1001 both extend beyond the end heads of one end of the first-layer chip 1 and one end of the second-layer chip 2 on the front surface of the third-layer chip 3 and form a first detection end 1201 that is connected to a detection instrument.

One end of the second reference electrode 1002 and one end of the second working electrode 1102 are both located within the detection chambers 9, and the other end of the second reference electrode 1002 and the other end of the second working electrode 1102 both extend beyond the end heads of one end of the fourth-layer chip 4 and one end of the fifth-layer chip 5 on the back surface of the third-layer chip 3 and form a second detection end 1202 that is connected to the detection instrument. That is, the first-layer chip 1 is flush with the end head of the second-layer chip 2 and with the end heads of the fourth-layer chip 4 and the fifth-layer chip 5, and the first detection end 1201 and the second detection end 1202 formed on the third-layer chip 3 are both exposed on the end heads of the first-layer chip 1 and the second-layer chip 2 and the end heads of the fourth-layer chip 4 and the fifth-layer chip 5.

Every two adjacent branching microfluidic channels 602 among the plurality of branching microfluidic channels 602 corresponding to the main flow channel 601 are of different lengths, so that the plurality of detection chambers 9 to which the plurality of adjacent branching microfluidic channels 602 are connected are arranged in a staggered distribution. Such a setting can decrease the size of the multi-channel microfluidic blood coagulation detection chip having a five-layer structure and lower the cost.

The second-layer chip 2 is provided with a first liquid receiving port 201, the third-layer chip 3 is provided with a second liquid receiving port 301, the fourth-layer chip 4 is provided with a third liquid receiving port 401, and the first liquid receiving port 201, the second liquid receiving port 301 and the third liquid receiving port 401 are all arranged corresponding to the position of the sample loading hole 8 and all communicate with the sample loading hole 8. The first main flow channel 601 includes a first main flow channel 6011 and a second main flow channel 6012. Each branching microfluidic channel 602 includes a first branching microfluidic channel 6021 and a second branching microfluidic channel 6022. The first main flow channel 6011 and the first branching microfluidic channel 6021 run through the second-layer chip 2. The second main flow channel 6012 and the second branching microfluidic channel 6022 run through the fourth-layer chip 4. One end of the first main flow channel 6011 is connected to the first liquid receiving port 201, and the other end of the first main flow channel 6011 is connected to the plurality of detection chambers 9 through a plurality of the first branching microfluidic channels 6021 in one-to-one correspondence. One end of the second main flow channel 6012 is connected to the third liquid receiving port 401, and the other end of the second main flow channel 6012 is connected to the plurality of detection chambers 9 through a plurality of the second branching microfluidic channels 6022 in one-to-one correspondence.

After entering the chip through the sample loading hole 8, a test blood sample flows to the first main flow channel 6011 and the second liquid receiving port 301 separately through the first liquid receiving port 201, flows to the third liquid receiving port 401 through the second liquid receiving port 301, and flows to the second main flow channel 6012 through the third liquid receiving port 401, so as to simultaneously flow to the detection chambers of the second-layer chip 2 and the detection chambers 9 of the fourth-layer chip 4, separately.

The first main flow channel 6011 extends in a horizontal direction to the end away from the first liquid receiving port 201 to be provided with a first part of the first branching microfluidic channel that is connected to a first detection chamber. The first main flow channel 6011 extends in a vertical direction to the end away from the first liquid receiving port 201 towards both sides respectively to be provided with a second part of the first branching microfluidic channel and a third part of the first branching microfluidic channel. The second part of the first branching microfluidic channel extends in a direction parallel to the first main flow channel 6011 to both ends respectively to connect to a second detection chamber and a third detection chamber. The third part of the first branching microfluidic channel extends in the direction parallel to the first main flow channel 6011 to both ends respectively to connect to a fourth detection chamber and a fifth detection chamber.

The second main flow channel 6012 extends in a horizontal direction to the end away from the third liquid receiving port 401 to be provided with a first part of the second branching microfluidic channel that is connected to a sixth detection chamber. The second main flow channel 6012 extends in a vertical direction to the end away from the third liquid receiving port 401 towards both sides respectively to be provided with a second part of the second branching microfluidic channel and a third part of the second branching microfluidic channel. The second part of the second branching microfluidic channel extends in a direction parallel to the second main flow channel 6012 to both ends respectively to connect to a seventh detection chamber and an eighth detection chamber. The third part of the second branching microfluidic channel extends in the direction parallel to the second main flow channel 6012 to both ends respectively to connect to a ninth detection chamber and a tenth detection chamber. That is, the number of the detection chambers 9 of the second-layer chip 2 is five, the number of the detection chambers 9 on the fourth-layer chip 4 is five, and the number of the detection chambers 9 of the multi-channel microfluidic blood coagulation detection chip having a five-layer structure is 10.

The sizes of the first liquid receiving port 201, the second liquid receiving port 301, and the third liquid receiving port 401 are all greater than or equal to the size of the sample loading hole 8. The plurality of vent holes 7 are all disposed above positions tangent to the tail ends of the plurality of detection chambers 9. The number of the vent holes 7 on both the first-layer chip 1 and the fifth-layer chip 5 is five. The tail ends of the detection chambers 9 are the ends far away from the branching microfluidic channels 602, and each detection chamber 9 is provided with a vent hole 7. The shape of each of the detection ends 12 is rectangular, and the spacing among the detection ends 12 is equal.

Figure 6:
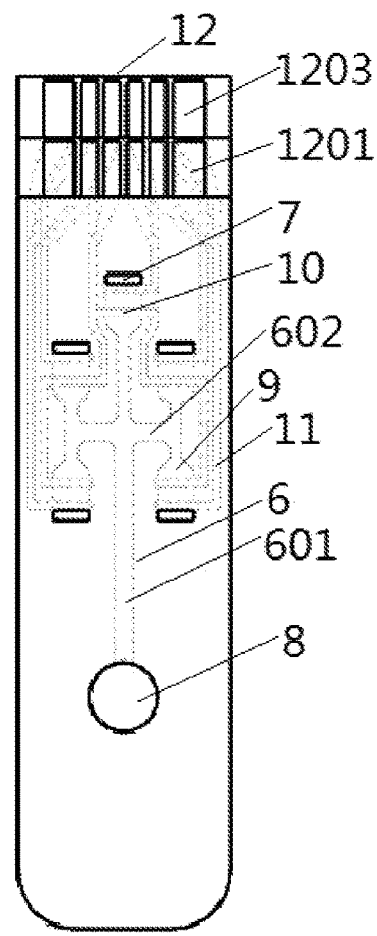
FIG. 6 is a schematic perspective structural diagram of a multi-channel microfluidic blood coagulation detection chip having a five-layer structure according to embodiment 2 of the present invention.
Figure 7:
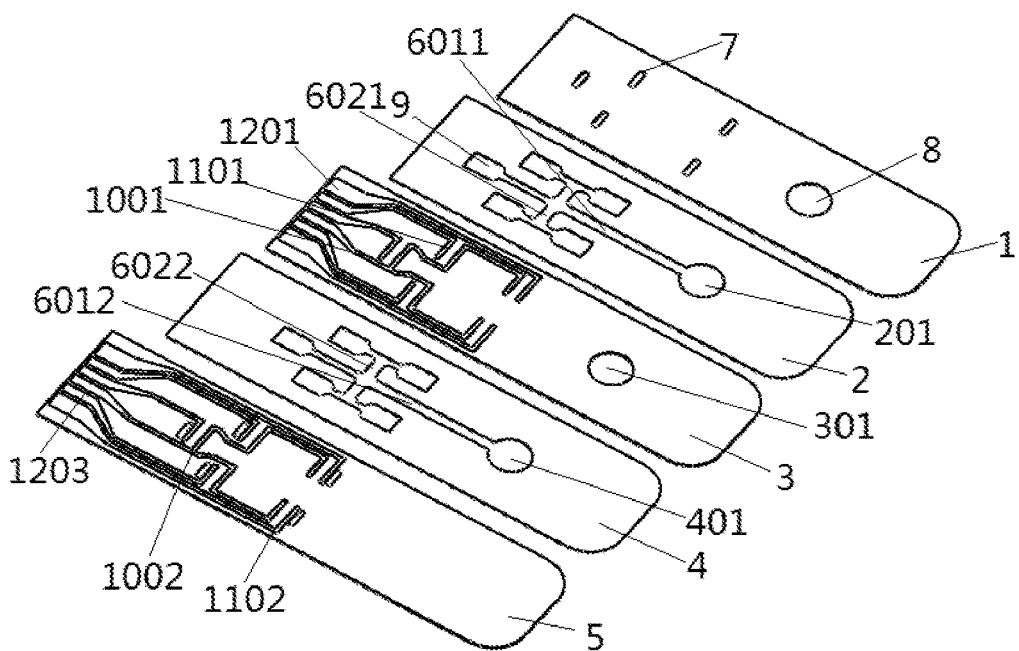
FIG. 7 is a schematic exploded structural diagram of chips of the multi-channel microfluidic blood coagulation detection chip having a five-layer structure according to embodiment 2 of the present invention.
Figure 8:
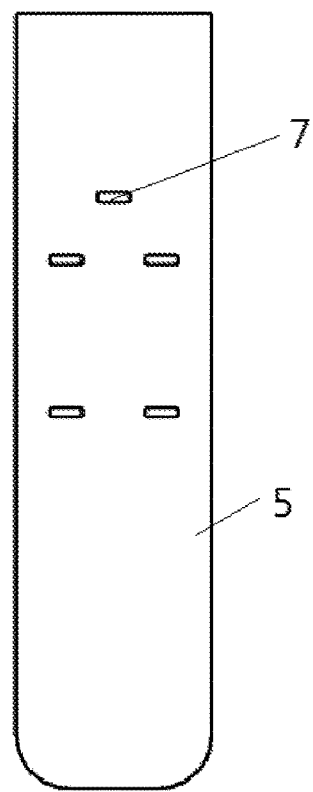
FIG. 8 is a schematic structural diagram of the back surface of the multi-channel microfluidic blood coagulation detection chip having a five-layer structure according to embodiment 2 of the present invention.
Figure 9:
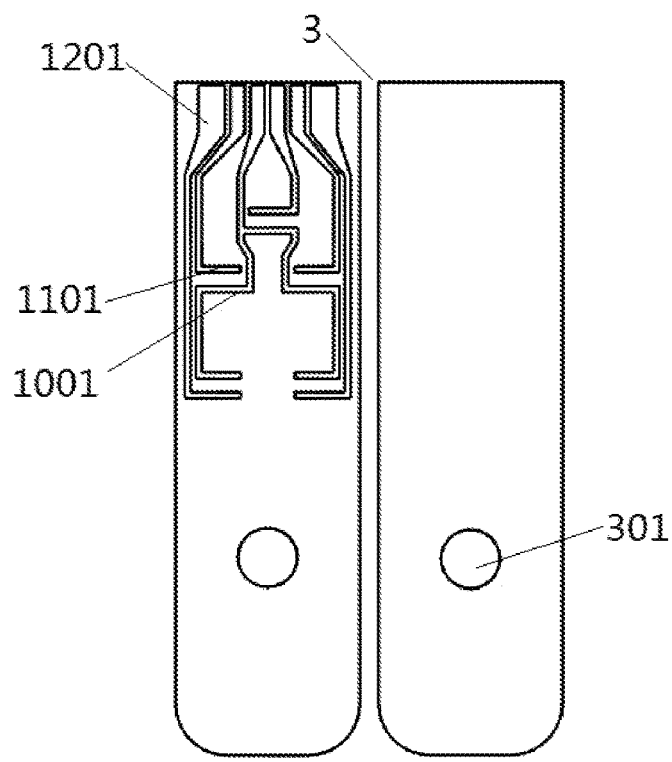
FIG. 9 is a schematic exploded structural diagram of the front surface and the back surface of a third-layer chip of the multi-channel microfluidic blood coagulation detection chip having a five-layer structure according to embodiment 2 of the present invention.
Figure 10:
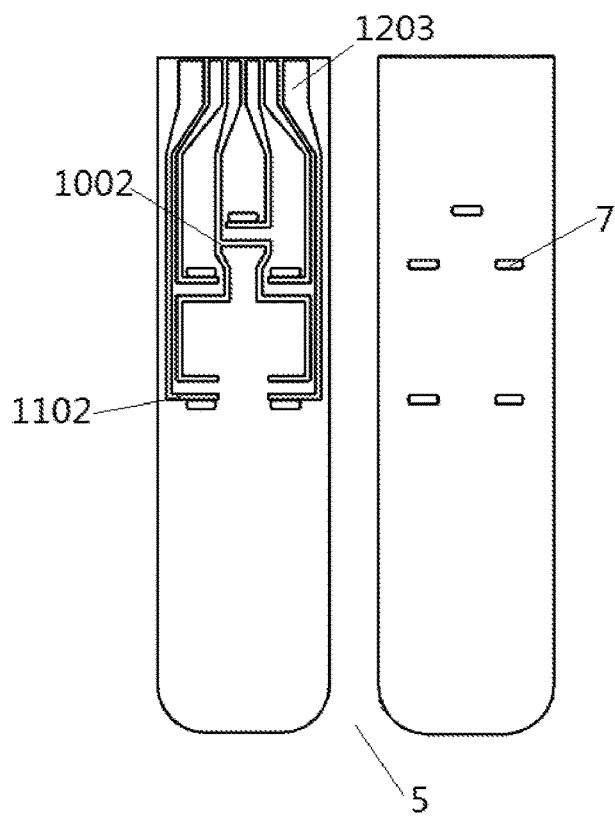
FIG. 10 is a schematic exploded structural diagram of the front surface and the back surface of a fifth-layer chip of the multi-channel microfluidic blood coagulation detection chip having a five-layer structure according to embodiment 2 of the present invention.

Embodiment 2. As shown in FIG. 6 to FIG. 10, this embodiment is different from embodiment 1 in that the second working electrode 1102 and the second reference electrode 1002 are disposed on the front surface of the fifth-layer chip 5. Specifically, the multi-channel microfluidic blood coagulation detection chip having a five-layer structure includes a chip body. The chip body includes, in sequence from top to bottom, a first-layer chip 1, a second-layer chip 2, a third-layer chip 3, a fourth-layer chip 4, and a fifth-layer chip 5. The first-layer chip 1, the second-layer chip 2, the third-layer chip 3, the fourth-layer chip 4, and the fifth-layer chip 5 cooperate with each other to define a closed microfluidic channel and a plurality of mutually-independent detection chambers 9. The first-layer chip 1 is provided with a sample loading hole 8, and the sample loading hole 8 communicates with the detection chambers 9 through the microfluidic channel 6. The chip body further includes electrodes, and the electrodes are disposed within the detection chambers 9 in one-to-one correspondence.

Both the microfluidic channel 6 and the detection chambers 9 run through the second-layer chip 2 and the fourth-layer chip 4. The microfluidic channel 6 includes a main flow channel 601 and a plurality of branching microfluidic channels 602, the tail end of the main flow channel 601 is divided into the plurality of branching microfluidic channels 602, and the plurality of branching microfluidic channels 602 communicate in one-to-one correspondence with the plurality of mutually-independent detection chambers 9. The front end of the main flow channel 601 communicates with the sample loading hole 8. Each detection chamber 9 is formed by a branching microfluidic channel 602 extending to both ends outwards on the tail end thereof, that is, the width of the detection chamber 9 is greater than the width of the branching microfluidic channel 602 connected thereto. Such a setting allows test the sample to flow to the detection chambers 9 easier and faster. Moreover, detection reagents are pre-embedded in the detection chambers 9.

Both the first-layer chip 1 and the fifth-layer chip 5 are provided with a plurality of vent holes 7, and the plurality of vent holes 7 are all disposed in one ends of the first-layer chip 1 and the fifth-layer chip 5 at positions corresponding to the detection chambers 9 and correspond one-to-one to the plurality of detection chambers 9.

The electrodes are disposed on the third-layer chip 3 and the fifth-layer chip 5. The electrodes include reference electrodes 10 and working electrodes 11, and the reference electrodes 10 and the working electrodes 11 are disposed within the detection chambers 9 in one-to-one correspondence.

Both the working electrodes 11 and the reference electrodes 10 are disposed on the third-layer chip 3 and the fifth-layer chip 5. One ends of both the working electrodes 11 and the reference electrodes 10 are located within the detection chambers 9, and the other ends of both the working electrodes 11 and the reference electrodes 10 extend to end heads of the third-layer chip 3 and the fifth-layer chip 5 to form detection ends 12. The plurality of detection chambers 9 corresponding to the branching microfluidic channels 602 are each independently provided therein with one of the working electrodes 11, which are independently led out to the detection ends 12. The reference electrodes 10 in the plurality of detection chambers 9 corresponding to the branching microfluidic channels 602 are all connected together in series and then led out to the detection ends 12. Both the reference electrodes 10 and the working electrodes 11 are rectangular at the detection ends 12 and arranged flush with the end heads of the third-layer chip 3 and/or the fifth-layer chip 5.

The reference electrodes 10 include a first reference electrode 1001 and a second reference electrode 1002, the first reference electrode 1001 is separated from the second reference electrode 1002, the first reference electrode 1001 is disposed on the front surface of the third-layer chip 3, and the second reference electrode 1002 is disposed on the front surface of the fifth-layer chip 5.

The working electrodes 11 include a first working electrode 1101 and a second working electrode 1102, the first working electrode 1101 is separated from the second working electrode 1102, the first working electrode 1101 is disposed on the front surface of the third-layer chip 3, and the second working electrode 1102 is disposed on the front surface of the fifth-layer chip 5.

One end of the first working electrode 1101 and one end of the first reference electrode 1001 are both located within the detection chambers 9 on the front surface of the third-layer chip 3, and the other end of first working electrode 1101 and the other end of the first reference electrode 1001 both extend beyond the end heads of one end of the first-layer chip 1 and one end of the second-layer chip 2 on the front surface of the third-layer chip 3 and form a first detection end 1201 that is connected to a detection instrument. The other end of the second reference electrode 1002 and the other end of the second working electrode 1102 both extend beyond the end heads of one end of the third-layer chip 3 and one end of the fourth-layer chip 4 on the front surface of the fifth-layer chip 5 and form a third detection end 1203 that is connected to the detection instrument.

The third detection end 1203 is exposed outside the end head of the detection terminal one 1201, that is, the first-layer chip 1 is flush with the second-layer chip 2, the third-layer chip 3 is flushed with the fourth-layer chip 4, the first detection end 1201 formed on the third-layer chip 3 is exposed outside the end heads of the first-layer chip 1 and the second-layer chip 2, and the third detection end 1203 formed on the fifth-layer chip 5 is exposed outside the end heads of the third-layer chip 3 and the fourth-layer chip 4. Such a layered setting can avoid interference between the first working electrode 1101 as well as the first reference electrode 1001 on the third-layer chip 3 and the second working electrode 1102 as well as the second reference electrode 1002 on the fifth-layer chip 5, and enable the first detection end 1201 and the third detection end 1203 of the multi-channel microfluidic blood coagulation detection chip having a five-layer structure to be directly connected to the detection instrument simultaneously after the detection chip is inserted into the detection instrument.

Every two adjacent branching microfluidic channels 602 among the plurality of branching microfluidic channels 602 corresponding to the main flow channel 601 are of different lengths, so that the plurality of detection chambers 9 to which the plurality of adjacent branching microfluidic channels 602 are connected are arranged in a staggered distribution. Such a setting can decrease the size of the chip body and lower the cost.

The second-layer chip 2 is provided with a first liquid receiving port 201, the third-layer chip 3 is provided with a second liquid receiving port 301, the fourth-layer chip 4 is provided with a third liquid receiving port 401, and the first liquid receiving port 201, the second liquid receiving port 301 and the third liquid receiving port 401 are all arranged corresponding to the position of the sample loading hole 8 and all communicate with the sample loading hole 8. The first main flow channel 601 includes a first main flow channel 6011 and a second main flow channel 6012. Each branching microfluidic channel 602 includes a first branching microfluidic channel 6021 and a second branching microfluidic channel 6022. The first main flow channel 6011 and the first branching microfluidic channel 6021 run through the second-layer chip 2. The second main flow channel 6012 and the second branching microfluidic channel 6022 run through the fourth-layer chip 4. One end of the first main flow channel 6011 is connected to the first liquid receiving port 201, and the other end of the first main flow channel 6011 is connected to the plurality of detection chambers 9 through a plurality of the first branching microfluidic channels 6021 in one-to-one correspondence. One end of the second main flow channel 6012 is connected to the third liquid receiving port 401, and the other end of the second main flow channel 6012 is connected to the plurality of detection chambers 9 through a plurality of the second branching microfluidic channels 6022 in one-to-one correspondence. After entering the chip through the sample loading hole 8, a test sample flows to the first main flow channel 6011 and the second liquid receiving port 301 separately through the first liquid receiving port 201, flows to the third liquid receiving port 401 through the second liquid receiving port 301, and flows to the second main flow channel 6012 through the third liquid receiving port 401, so as to simultaneously flow to the detection chambers of the second-layer chip 2 and the detection chambers 9 of the fourth-layer chip 4, separately. The first main flow channel 6011 extends in a horizontal direction to the end away from the first liquid receiving port 201 to be provided with a first part of the first branching microfluidic channel that is connected to a first detection chamber. The first main flow channel 6011 extends in a vertical direction to the end away from the first liquid receiving port 201 towards both sides respectively to be provided with a second part of the first branching microfluidic channel and a third part of the first branching microfluidic channel. The second part of the first branching microfluidic channel extends in a direction parallel to the first main flow channel 6011 to both ends respectively to connect to a second detection chamber and a third detection chamber. The third part of the first branching microfluidic channel extends in the direction parallel to the first main flow channel 6011 to both ends respectively to connect to a fourth detection chamber and a fifth detection chamber.

The second main flow channel 6012 extends in a horizontal direction to the end away from the third liquid receiving port 401 to be provided with a first part of the second branching microfluidic channel that is connected to a sixth detection chamber. The second main flow channel 6012 extends in a vertical direction to the end away from the third liquid receiving port 401 towards both sides respectively to be provided with a second part of the second branching microfluidic channel and a third part of the second branching microfluidic channel. The second part of the second branching microfluidic channel extends in a direction parallel to the second main flow channel 6012 to both ends respectively to connect to a seventh detection chamber and an eighth detection chamber. The third part of the second branching microfluidic channel extends in the direction parallel to the second main flow channel 6012 to both ends respectively to connect to a ninth detection chamber and a tenth detection chamber. That is, the number of the detection chambers 9 of the second-layer chip 2 is five, the number of the detection chambers 9 on the fourth-layer chip 4 is five, and the number of the detection chambers 9 of the multi-channel microfluidic blood coagulation detection chip having a five-layer structure is 10.

The sizes of the first liquid receiving port 201, the second liquid receiving port 301, and the third liquid receiving port 401 are all greater than or equal to the size of the sample loading hole 8. The plurality of vent holes 7 are all disposed above positions tangent to the tail ends of the plurality of detection chambers 9. The number of the vent holes 7 on both the first-layer chip 1 and the fifth-layer chip 5 is five. The tail ends of the detection chambers 9 are the ends far away from the branching microfluidic channels 602, and each detection chamber 9 is provided with a vent hole 7. The shape of each of the detection ends 12 is rectangular, and the spacing among the detection ends 12 is equal.

Embodiment 3. The multi-channel microfluidic blood coagulation detection chip having a five-layer structure includes a chip body. The chip body includes, in sequence from top to bottom, a first-layer chip 1, a second-layer chip 2, a third-layer chip 3, a fourth-layer chip 4, and a fifth-layer chip 5. The first-layer chip 1, the second-layer chip 2, the third-layer chip 3, the fourth-layer chip 4, and the fifth-layer chip 5 cooperate with each other to define a closed microfluidic channel and a plurality of mutually-independent detection chambers 9. The first-layer chip 1 is provided with a sample loading hole 8, and the sample loading hole 8 communicates with the detection chambers 9 through the microfluidic channel 6. The chip body further includes electrodes, and the electrodes are disposed within the detection chambers 9 in one-to-one correspondence. Both the microfluidic channel 6 and the detection chambers 9 run through the second-layer chip 2 and the fourth-layer chip 4. The microfluidic channel 6 includes a main flow channel 601 and a plurality of branching microfluidic channels 602, the tail end of the main flow channel 601 is divided into the plurality of branching microfluidic channels 602, and the plurality of branching microfluidic channels 602 communicate in one-to-one correspondence with the plurality of mutually-independent detection chambers 9. The front end of the main flow channel 601 communicates with the sample loading hole 8. Each detection chamber 9 is formed by a branching microfluidic channel 602 extending to both ends outwards on the tail end thereof, that is, the width of the detection chamber 9 is greater than the width of the branching microfluidic channel 602 connected thereto. Such a setting allows the test sample to flow to the detection chambers 9 easier and faster. Moreover, detection reagents are pre-embedded in the detection chambers 9. Both the first-layer chip 1 and the fifth-layer chip 5 are provided with a plurality of vent holes 7, and the plurality of vent holes 7 are all disposed in one ends of the first-layer chip 1 and the fifth-layer chip 5 at positions corresponding to the detection chambers 9 and correspond one-to-one to the plurality of detection chambers 9. The electrodes are disposed on the third-layer chip 3. The electrodes include reference electrodes 10 and working electrodes 11, and the reference electrodes 10 and the working electrodes 11 are disposed within the detection chambers 9 in one-to-one correspondence. Both the working electrodes 11 and the reference electrodes 10 are disposed on the third-layer chip 3. One ends of both the working electrodes 11 and the reference electrodes 10 are located within the detection chambers 9, and the other ends of both the working electrodes 11 and the reference electrodes 10 extend to an end head of the third-layer chip 3 to form detection ends 12. The plurality of detection chambers 9 corresponding to the branching microfluidic channels 602 are each independently provided therein with one of the working electrodes 11, which are independently led out to the detection ends 12. The reference electrodes 10 in the plurality of detection chambers 9 corresponding to the branching microfluidic channels 602 are all connected together in series and then led out to the detection ends 12. Both the reference electrodes 10 and the working electrodes 11 are rectangular at the detection ends 12 and arranged flush with the end head of the third-layer chip 3. The reference electrodes 10 include a first reference electrode 1001 and a second reference electrode 1002, the first reference electrode 1001 is separated from the second reference electrode 1002, the first reference electrode 1001 is disposed on the front surface of the third-layer chip 3, and the second reference electrode 1002 is disposed on the back surface of the third-layer chip 3. The working electrodes 11 include a first working electrode 1101 and a second working electrode 1102, the first working electrode 1101 is separated from the second working electrode 1102, the first working electrode 1101 is disposed on the front surface of the third-layer chip 3, and the second working electrode 1102 is disposed on the back surface of the third-layer chip 3. One end of the first working electrode 1101 and one end of the first reference electrode 1001 are both located within the detection chambers 9 on the front surface of the third-layer chip 3, and the other end of first working electrode 1101 and the other end of the first reference electrode 1001 both extend beyond the end heads of one end of the first-layer chip 1 and one end of the second-layer chip 2 on the front surface of the third-layer chip 3 and form a first detection end 1201 that is connected to a detection instrument. One end of the second reference electrode 1002 and one end of the second working electrode 1102 are both located within the detection chambers 9, and the other end of the second reference electrode 1002 and the other end of the second working electrode 1102 both extend beyond the end heads of one end of the fourth-layer chip 4 and one end of the fifth-layer chip 5 on the back surface of the third-layer chip 3 and form a second detection end 1202 that is connected to the detection instrument. That is, the first-layer chip 1 is flush with the end head of the second-layer chip 2 and with the end heads of the fourth-layer chip 4 and the fifth-layer chip 5, and the first detection end 1201 and the second detection end 1202 formed on the third-layer chip 3 are both exposed on the end heads of the first-layer chip 1 and the second-layer chip 2 and the end heads of the fourth-layer chip 4 and the fifth-layer chip 5. Every two adjacent branching microfluidic channels 602 extending in the same direction among the plurality of branching microfluidic channels 602 corresponding to the main flow channel 601 are of different lengths, so that the plurality of detection chambers 9 to which the plurality of adjacent branching microfluidic channels 602 in the same direction are connected are arranged in a staggered distribution. Such a setting can decrease the size of the chip body and lower the cost.

The second-layer chip 2 is provided with a first liquid receiving port 201, the third-layer chip 3 is provided with a second liquid receiving port 301, the fourth-layer chip 4 is provided with a third liquid receiving port 401, and the first liquid receiving port 201, the second liquid receiving port 301 and the third liquid receiving port 401 are all arranged corresponding to the position of the sample loading hole 8 and all communicate with the sample loading hole 8. The first main flow channel 601 includes a first main flow channel 6011 and a second main flow channel 6012. Each branching microfluidic channel 602 includes a first branching microfluidic channel 6021 and a second branching microfluidic channel 6022. The first main flow channel 6011 and the first branching microfluidic channel 6021 run through the second-layer chip 2. The second main flow channel 6012 and the second branching microfluidic channel 6022 run through the fourth-layer chip 4. One end of the first main flow channel 6011 is connected to the first liquid receiving port 201, and the other end of the first main flow channel 6011 is connected to the plurality of detection chambers 9 through a plurality of the first branching microfluidic channels 6021 in one-to-one correspondence. One end of the second main flow channel 6012 is connected to the third liquid receiving port 401, and the other end of the second main flow channel 6012 is connected to the plurality of detection chambers 9 through a plurality of the second branching microfluidic channels 6022 in one-to-one correspondence. After entering the chip through the sample loading hole 8, a test sample flows to the first main flow channel 6011 and the second liquid receiving port 301 separately through the first liquid receiving port 201, flows to the third liquid receiving port 401 through the second liquid receiving port 301, and flows to the second main flow channel 6012 through the third liquid receiving port 401, so as to simultaneously flow to the detection chambers of the second-layer chip 2 and the detection chambers 9 of the fourth-layer chip 4, separately. The first main flow channel 6011 extends in a horizontal direction to the end away from the first liquid receiving port 201 to be provided with a first part of the first branching microfluidic channel that is connected to a first detection chamber. The first main flow channel 6011 extends in a vertical direction to the end away from the first liquid receiving port 201 towards both sides respectively to be provided with a second part of the first branching microfluidic channel and a third part of the first branching microfluidic channel. The second part of the first branching microfluidic channel extends in a direction parallel to the first main flow channel 6011 to both ends respectively to connect to a second detection chamber and a third detection chamber. The third part of the first branching microfluidic channel extends in the direction parallel to the first main flow channel 6011 to both ends respectively to connect to a fourth detection chamber and a fifth detection chamber.

The second main flow channel 6012 extends in a horizontal direction to the end away from the third liquid receiving port 401 to be provided with a first part of the second branching microfluidic channel that is connected to a sixth detection chamber. The second main flow channel 6012 extends in a vertical direction to the end away from the third liquid receiving port 401 towards both sides respectively to be provided with a second part of the second branching microfluidic channel and a third part of the second branching microfluidic channel. The second part of the second branching microfluidic channel extends in a direction parallel to the second main flow channel 6012 to both ends respectively to connect to a seventh detection chamber and an eighth detection chamber. The third part of the second branching microfluidic channel extends in the direction parallel to the second main flow channel 6012 to both ends respectively to connect to a fourth detection chamber and a fifth detection chamber. That is, the number of the detection chambers 9 of the second-layer chip 2 is five, the number of the detection chambers 9 on the fourth-layer chip 4 is five, and the number of the detection chambers 9 of the multi-channel microfluidic blood coagulation detection chip having a five-layer structure is 10. The sizes of the first liquid receiving port 201, the second liquid receiving port 301, and the third liquid receiving port 401 are all greater than or equal to the size of the sample loading hole 8. The plurality of vent holes 7 are all disposed above positions tangent to the tail ends of the plurality of detection chambers 9. The number of the vent holes 7 on both the first-layer chip 1 and the fifth-layer chip 5 is five. The tail ends of the detection chambers 9 are the ends far away from the branching microfluidic channels 602, and each detection chamber 9 is provided with a vent hole 7. The shape of each of the detection ends 12 is rectangular, and the spacing among the detection ends 12 is equal. The first-layer chip 1, the second-layer chip 2, the third-layer chip 3, the fourth-layer chip 4, and the fifth-layer chip 5 are bonded into an integral whole by means of gluing. The second-layer chip 2 and the fourth-layer chip 4 are pressure-sensitive adhesive tapes. The materials of the first-layer chip 1, the third-layer chip 3 and the fifth-layer chip 5 are all any one of PMMA, PP, PE, and PET, and the surfaces of the first-layer chip 1 and the fifth-layer chip 5 each are provided with a hydrophilic membrane, so that the sample quickly flows through the sample loading hole 8 into the main flow channel, and then separately flows to each branching microfluidic channel 602. The thicknesses of the second-layer chip 2 and the fourth-layer chip 4 are both 0.1~1.0 mm. The depths of the closed microfluidic channels 6 defined by the first-layer chip 1, the second-layer chip 2 and the front surface of the third-layer chip 3 and by the fourth-layer chip 4, the fifth-layer chip 5 and the back surface of the third-layer chip 3 in cooperation are both 0.1~1.0 mm, and the widths of the detection chambers 9 defined by the five layers of chips in cooperation are all 1.0~2.0 mm. Each of the branching microfluidic channels 602 is provided with a nozzle at a junction with the detection chamber 9, and the thickness of the electrodes is 0.5 mm.

Embodiment 4. The multi-channel microfluidic blood coagulation detection chip having a five-layer structure includes a chip body. The chip body includes, in sequence from top to bottom, a first-layer chip 1, a second-layer chip 2, a third-layer chip 3, a fourth-layer chip 4, and a fifth-layer chip 5. The first-layer chip 1, the second-layer chip 2, the third-layer chip 3, the fourth-layer chip 4, and the fifth-layer chip 5 cooperate with each other to define a closed microfluidic channel and a plurality of mutually-independent detection chambers 9. The first-layer chip 1 is provided with a sample loading hole 8, and the sample loading hole 8 communicates with the detection chambers 9 through the microfluidic channel 6. The chip body further includes electrodes, and the electrodes are disposed within the detection chambers 9 in one-to-one correspondence. Both the microfluidic channel 6 and the detection chambers 9 run through the second-layer chip 2 and the fourth-layer chip 4. The microfluidic channel 6 includes a main flow channel 601 and a plurality of branching microfluidic channels 602, the tail end of the main flow channel 601 is divided into the plurality of branching microfluidic channels 602, and the plurality of branching microfluidic channels 602 communicate in one-to-one correspondence with the plurality of mutually-independent detection chambers 9. The front end of the main flow channel 601 communicates with the sample loading hole 8. Each detection chamber 9 is formed by a branching microfluidic channel 602 extending to both ends outwards on the tail end thereof, that is, the width of the detection chamber 9 is greater than the width of the branching microfluidic channel 602 connected thereto. Such a setting allows the test sample to flow to the detection chambers 9 easier and faster. Moreover, detection reagents are pre-embedded in the detection chambers 9. Both the first-layer chip 1 and the fifth-layer chip 5 are provided with a plurality of vent holes 7, and the plurality of vent holes 7 are all disposed in one ends of the first-layer chip 1 and the fifth-layer chip 5 at positions corresponding to the detection chambers 9 and correspond one-to-one to the plurality of detection chambers 9. The electrodes are disposed on the third-layer chip 3 and the fifth-layer chip 5. The electrodes include reference electrodes 10 and working electrodes 11, and the reference electrodes 10 and the working electrodes 11 are disposed within the detection chambers 9 in one-to-one correspondence. Both the working electrodes 11 and the reference electrodes 10 are disposed on the third-layer chip 3 and the fifth-layer chip 5. One ends of both the working electrodes 11 and the reference electrodes 10 are located within the detection chambers 9, and the other ends of both the working electrodes 11 and the reference electrodes 10 extend to end heads of the third-layer chip 3 and the fifth-layer chip 5 to form detection ends 12. The plurality of detection chambers 9 corresponding to the branching microfluidic channels 602 are each independently provided therein with one of the working electrodes 11, which are independently led out to the detection ends 12. The reference electrodes 10 in the plurality of detection chambers 9 corresponding to the branching microfluidic channels 602 are all connected together in series and then led out to the detection ends 12. Both the reference electrodes 10 and the working electrodes 11 are rectangular at the detection ends 12 and arranged flush with the end heads of the third-layer chip 3 and/or the fifth-layer chip 5. The reference electrodes 10 include a first reference electrode 1001 and a second reference electrode 1002, the first reference electrode 1001 is separated from the second reference electrode 1002, the first reference electrode 1001 is disposed on the front surface of the third-layer chip 3, and the second reference electrode 1002 is disposed on the front surface of the fifth-layer chip 5. The working electrodes 11 include a first working electrode 1101 and a second working electrode 1102, the first working electrode 1101 is separated from the second working electrode 1102, the first working electrode 1101 is disposed on the front surface of the third-layer chip 3, and the second working electrode 1102 is disposed on the front surface of the fifth-layer chip 5. One end of the first working electrode 1101 and one end of the first reference electrode 1001 are both located within the detection chambers 9 on the front surface of the third-layer chip 3, and the other end of first working electrode 1101 and the other end of the first reference electrode 1001 both extend beyond the end heads of one end of the first-layer chip 1 and one end of the second-layer chip 2 on the front surface of the third-layer chip 3 and form a first detection end 1201 that is connected to a detection instrument. The other end of the second reference electrode 1002 and the other end of the second working electrode 1102 both extend beyond the end heads of one end of the third-layer chip 3 and one end of the fourth-layer chip 4 on the front surface of the fifth-layer chip 5 and form a third detection end 1203 that is connected to the detection instrument. The third detection end 1203 is exposed outside the end head of the detection terminal one 1201, that is, the first-layer chip 1 is flush with the second-layer chip 2, the third-layer chip 3 is flushed with the fourth-layer chip 4, the first detection end 1201 formed on the third-layer chip 3 is exposed outside the end heads of the first-layer chip 1 and the second-layer chip 2, and the third detection end 1203 formed on the fifth-layer chip 5 is exposed outside the end heads of the third-layer chip 3 and the fourth-layer chip 4. Such a layered setting can avoid interference between the first working electrode 1101 as well as the first reference electrode 1001 on the third-layer chip 3 and the second working electrode 1102 as well as the second reference electrode 1002 on the fifth-layer chip 5, and enable the first detection end 1201 and the third detection end 1203 of the multi-channel microfluidic blood coagulation detection chip having a five-layer structure to be directly connected to the detection instrument simultaneously after the detection chip is inserted into the detection instrument. Every two adjacent branching microfluidic channels 602 extending in the same direction among the plurality of branching microfluidic channels 602 corresponding to the main flow channel 601 are of different lengths, so that the plurality of detection chambers 9 to which the plurality of adjacent branching microfluidic channels 602 in the same direction are connected are arranged in a staggered distribution. Such a setting can decrease the size of the chip body and lower the cost.

The second-layer chip 2 is provided with a first liquid receiving port 201, the third-layer chip 3 is provided with a second liquid receiving port 301, the fourth-layer chip 4 is provided with a third liquid receiving port 401, and the first liquid receiving port 201, the second liquid receiving port 301 and the third liquid receiving port 401 are all arranged corresponding to the position of the sample loading hole 8 and all communicate with the sample loading hole 8. The first main flow channel 601 includes a first main flow channel 6011 and a second main flow channel 6012. Each branching microfluidic channel 602 includes a first branching microfluidic channel 6021 and a second branching microfluidic channel 6022. The first main flow channel 6011 and the first branching microfluidic channel 6021 run through the second-layer chip 2. The second main flow channel 6012 and the second branching microfluidic channel 6022 run through the fourth-layer chip 4. One end of the first main flow channel 6011 is connected to the first liquid receiving port 201, and the other end of the first main flow channel 6011 is connected to the plurality of detection chambers 9 through a plurality of the first branching microfluidic channels 6021 in one-to-one correspondence. One end of the second main flow channel 6012 is connected to the third liquid receiving port 401, and the other end of the second main flow channel 6012 is connected to the plurality of detection chambers 9 through a plurality of the second branching microfluidic channels 6022 in one-to-one correspondence.

After entering the chip through the sample loading hole 8, a test sample flows to the first main flow channel 6011 and the second liquid receiving port 301 separately through the first liquid receiving port 201, flows to the third liquid receiving port 401 through the second liquid receiving port 301, and flows to the second main flow channel 6012 through the third liquid receiving port 401, so as to simultaneously flow to the detection chambers of the second-layer chip 2 and the detection chambers 9 of the fourth-layer chip 4, separately. The first main flow channel 6011 extends in a horizontal direction to the end away from the first liquid receiving port 201 to be provided with a first part of the first branching microfluidic channel that is connected to a first detection chamber. The first main flow channel 6011 extends in a vertical direction to the end away from the first liquid receiving port 201 towards both sides respectively to be provided with a second part of the first branching microfluidic channel and a third part of the first branching microfluidic channel. The second part of the first branching microfluidic channel extends in a direction parallel to the first main flow channel 6011 to both ends respectively to connect to a second detection chamber and a third detection chamber. The third part of the first branching microfluidic channel extends in the direction parallel to the first main flow channel 6011 to both ends respectively to connect to a fourth detection chamber and a fifth detection chamber.

The second main flow channel 6012 extends in a horizontal direction to the end away from the third liquid receiving port 401 to be provided with a first part of the second branching microfluidic channel that is connected to a sixth detection chamber. The second main flow channel 6012 extends in a vertical direction to the end away from the third liquid receiving port 401 towards both sides respectively to be provided with a second part of the second branching microfluidic channel and a third part of the second branching microfluidic channel. The second part of the second branching microfluidic channel extends in a direction parallel to the second main flow channel 6012 to both ends respectively to connect to a seventh detection chamber and an eighth detection chamber. The third part of the second branching microfluidic channel extends in the direction parallel to the second main flow channel 6012 to both ends respectively to connect to a ninth detection chamber and a tenth detection chamber. That is, the number of the detection chambers 9 of the second-layer chip 2 is five, the number of the detection chambers 9 on the fourth-layer chip 4 is five, and the number of the detection chambers 9 of the multi-channel microfluidic blood coagulation detection chip having a five-layer structure is 10.

The sizes of the first liquid receiving port 201, the second liquid receiving port 301, and the third liquid receiving port 401 are all greater than or equal to the size of the sample loading hole 8. The plurality of vent holes 7 are all disposed above positions tangent to the tail ends of the plurality of detection chambers 9. The number of the vent holes 7 on both the first-layer chip 1 and the fifth-layer chip 5 is five. The tail ends of the detection chambers 9 are the ends far away from the branching microfluidic channels 602, and each detection chamber 9 is provided with a vent hole 7.

The shape of each of the detection ends 12 is rectangular, and the spacing among the detection ends 12 is equal. The first-layer chip 1, the second-layer chip 2, the third-layer chip 3, the fourth-layer chip 4, and the fifth-layer chip 5 are bonded into an integral whole by means of gluing. The second-layer chip 2 and the fourth-layer chip 4 are pressure-sensitive adhesive tapes. The materials of the first-layer chip 1, the third-layer chip 3 and the fifth-layer chip 5 are all any one of PMMA, PP, PE, and PET, and the surfaces of the first-layer chip 1 and the fifth-layer chip 5 each are provided with a hydrophilic membrane, so that the sample quickly flows through the sample loading hole 8 into the main flow channel, and then separately flows to each branching microfluidic channel 602.

The thicknesses of the second-layer chip 2 and the fourth-layer chip 4 are both 0.1~1.0 mm. The depths of the closed microfluidic channels 6 defined by the first-layer chip 1, the second-layer chip 2 and the front surface of the third-layer chip 3 and by the fourth-layer chip 4, the fifth-layer chip 5 and the back surface of the third-layer chip 3 in cooperation are both 0.1~1.0 mm, and the widths of the detection chambers 9 defined by the five layers of chips in cooperation are all 1.0~2.0 mm. Each of the branching microfluidic channels 602 is provided with a nozzle at a junction with the detection chamber 9, and the thickness of the electrodes is 0.5 mm.

During specific use:

A test sample is injected into the sample loading hole 8. After entering the chip through the sample loading hole 8, the test sample separately flows to the first main flow channel 6011 and the second liquid receiving port 301 through the first liquid receiving port 201, flows to the third liquid receiving port 401 through the second liquid receiving port 301, and flows to the second main flow channel 6012 through the third liquid receiving port 401, so as to simultaneously flow to the detection chambers of the second-layer chip 2 and the detection chambers 9 of the fourth-layer chip 4, separately. The sample reacts with the detection reagents pre-embedded in the detection chambers 9. In addition, under the action of the first working electrode 1101 and the first reference electrode 1001 as well as the second working electrode 1102 and the second reference electrode 1002, an alternating-current resistance method is used to monitor changes of electrochemical signals generated by the reaction with a supporting detection instrument, to obtain detection results. In this way, 10 coagulation indexes can be detected simultaneously with one sample injection, thereby improving the detection efficiency.

The basic principles, major features and advantages of the present invention are shown and described above. A person skilled in the art should understand that the present invention is not limited by the foregoing embodiments. The foregoing embodiments and the description are descriptive to only illustrate the principles of the present invention. Various changes and improvements, such as some other slight adjustments of the shape and structure of the sample loading hole, or some adjustments of the arrangement mode and number of the detection chambers, can also made to the present invention, without departing from the spirit and the scope of the present invention. These changes and improvements all fall within the scope of protection of the present invention. The scope of protection claimed by the present invention is defined by the appended claims and equivalents thereof.

What is claimed is:

1. A multi-channel microfluidic chip having a five-layer structure, the detection chip comprising a chip body, wherein the chip body comprises a first-layer chip, a second-layer chip, a third-layer chip, a fourth-layer chip, and a fifth-layer chip arranged in sequence from top to bottom; the first-layer chip, the second-layer chip, the third-layer chip, the fourth-layer chip, and the fifth-layer chip cooperate with each other to define a closed microfluidic channel and a plurality of mutually-independent detection chambers; the first-layer chip is provided with a sample loading hole, and the sample loading hole communicates with the detection chambers through the microfluidic channel; and the chip body further comprises electrodes, and the electrodes are disposed within the detection chambers in one-to-one correspondence, wherein both the microfluidic channel and the detection chambers run through the second-layer chip and the fourth-layer chip;

the microfluidic channel comprises a main flow channel and a plurality of branching microfluidic channels, a tail end of the main flow channel is divided into the plurality of branching microfluidic channels, and the plurality of branching microfluidic channels communicate in one-to-one correspondence with the plurality of mutually-independent detection chambers; and a front end of the main flow channel communicates with the sample loading hole, the electrodes comprise reference electrodes and working electrodes, both the working electrodes and the reference electrodes are disposed on the third-layer chip and the fifth-layer chip; one ends of both the working electrodes and the reference electrodes are located within the detection chambers, and the other ends of both the working electrodes and the reference electrodes extend to end heads of the third-layer chip and the fifth-layer chip to form detection ends;

the plurality of detection chambers corresponding to the branching microfluidic channels are each independently provided therein with one of the working electrodes, which are independently led out to the detection ends; and the reference electrodes in the plurality of detection chambers corresponding to the branching microfluidic channels are all connected together in series and then led out to the detection ends, wherein every two adjacent branching microfluidic channels among the plurality of branching microfluidic channels corresponding to the main flow channel are of different lengths along an extension direction of the main flow channel.

2. The multi-channel microfluidic-chip having a five-layer structure according to claim 1, wherein both the first-layer chip and the fifth-layer chip are provided with a plurality of vent holes, and the plurality of vent holes are all disposed in one ends of the first-layer chip and the fifth-layer chip at positions corresponding to the detection chambers and correspond one-to-one to the plurality of detection chambers.

3. The multi-channel microfluidic chip having a five-layer structure according to claim 1, wherein the reference electrodes comprise a first reference electrode and a second reference electrode, the first reference electrode is separated from the second reference electrode, the first reference electrode is disposed on a front surface of the third-layer chip, and the second reference electrode is disposed on a back surface of the third-layer chip or a front surface of the fifth-layer chip.

4. The multi-channel microfluidic chip having a five-layer structure according to claim 3, wherein the working electrodes comprise a first working electrode and a second working electrode, the first working electrode is separated from the second working electrode, the first working electrode is disposed on the front surface of the third-layer chip, and the second working electrode is disposed on the back surface of the third-layer chip or the front surface of the fifth-layer chip.

5. The multi-channel microfluidic chip having a five-layer structure according to claim 4, wherein one end of the first working electrode and one end of the first reference electrode are both located within the detection chambers on the front surface of the third-layer chip; and the other end of first working electrode and the other end of the first reference electrode both extend beyond end heads of one end of the first-layer chip and one end of the second-layer chip on the front surface of the third-layer chip and form a first detection end that is connected to a detection instrument.

6. The multi-channel microfluidic-chip having a five-layer structure according to claim 5, wherein one end of the second reference electrode and one end of the second working electrode are both located within the detection chambers; and the other end of the second reference electrode and the other end of the second working electrode both extend beyond end heads of one end of the fourth-layer chip and one end of the fifth-layer chip on the back surface of the third-layer chip and form a second detection end that is connected to the detection instrument, or the other end of the second reference electrode and the other end of the second working electrode both extend beyond the end heads of one end of the third-layer chip and one end of the fourth-layer chip on the front surface of the fifth-layer chip and form a third detection end that is connected to the detection instrument.

7. The multi-channel microfluidic chip having a five-layer structure according to claim 6, wherein the third detection end is exposed outside an end head of the first detection end.

8. The multi-channel microfluidic chip having a five-layer structure according to claim 6, wherein the second-layer chip is provided with a first liquid receiving port, the third-layer chip is provided with a second liquid receiving port, the fourth-layer chip is provided with a third liquid receiving port, and the first liquid receiving port, the second liquid receiving port and the third liquid receiving port are all arranged corresponding to a position of the sample loading hole and all communicate with the sample loading hole; the first main flow channel comprises a first main flow channel and a second main flow channel; each branching microfluidic channel comprises a first branching microfluidic channel and a second branching microfluidic channel; the first main flow channel and the first branching microfluidic channel run through the second-layer chip; the second main flow channel and the second branching microfluidic channel run through the fourth-layer chip; one end of the first main flow channel is connected to the first liquid receiving port, and the other end of the first main flow channel is connected to the plurality of detection chambers through a plurality of the first branching microfluidic channels in one-to-one correspondence; and one end of the second main flow channel is connected to the third liquid receiving port, and the other end of the second main flow channel is connected to the plurality of detection chambers through a plurality of the second branching microfluidic channels in one-to-one correspondence.

9. The multi-channel microfluidic-chip having a five-layer structure according to claim 8, wherein the first main flow channel extends in a horizontal direction to an end away from the first liquid receiving port to be provided with a first part of the first branching microfluidic channel that is connected to a first detection chamber; the first main flow channel extends in a vertical direction to the end away from the first liquid receiving port towards both sides respectively to be provided with a second part of the first branching microfluidic channel and a third part of the first branching microfluidic channel; the second part of the first branching microfluidic channel extends in a direction parallel to the first main flow channel to both ends respectively to connect to a second detection chamber and a third detection chamber; and the third part of the first branching microfluidic channel extends in the direction parallel to the first main flow channel to both ends respectively to connect to a fourth detection chamber and a fifth detection chamber.

10. The multi-channel microfluidic chip having a five-layer structure according to claim 8, wherein the second main flow channel extends in a horizontal direction to an end away from the third liquid receiving port to be provided with a first part of the second branching microfluidic channel that is connected to a sixth detection chamber; the second main flow channel extends in a vertical direction to the end away from the third liquid receiving port towards both sides respectively to be provided with a second part of the second branching microfluidic channel and a third part of the second branching microfluidic channel; the second part of the second branching microfluidic channel extends in a direction parallel to the second main flow channel to both ends respectively to connect to a seventh detection chamber and an eighth detection chamber; and the third part of the second branching microfluidic channel extends in the direction parallel to the second main flow channel to both ends respectively to connect to a ninth detection chamber and a tenth detection chamber.

11. The multi-channel microfluidic chip having a five-layer structure according to claim 9, wherein sizes of the first liquid receiving port, the second liquid receiving port, and the third liquid receiving port are all greater than or equal to a size of the sample loading hole; the plurality of vent holes are all disposed above positions tangent to tail ends of the plurality of detection chambers; and a number of the vent holes on both the first-layer chip and the fifth-layer chip is five.

12. The multi-channel microfluidic chip having a five-layer structure according to claim 10, wherein sizes of the first liquid receiving port, the second liquid receiving port, and the third liquid receiving port are all greater than or equal to a size of the sample loading hole; the plurality of vent holes are all disposed above positions tangent to tail ends of the plurality of detection chambers; and a number of the vent holes on both the first-layer chip and the fifth-layer chip is five.

* * * * *